United States Patent [19]

Beck et al.

[11] 4,171,442

[45] Oct. 16, 1979

[54] PROCESS FOR THE PREPARATION OF 2,4,5-TRICHLOROPYRIMIDINE

[75] Inventors: Gunther Beck; Helmut Heitzer, both of Leverkusen, Fed. Rep. of Germany

[73] Assignee: Bayer Aktiengesellschaft, Leverkusen, Fed. Rep. of Germany

[21] Appl. No.: 913,119

[22] Filed: Jun. 6, 1978

[30] Foreign Application Priority Data

Jun. 8, 1977 [DE] Fed. Rep. of Germany ....... 2725888

[51] Int. Cl.$^2$ ........................................... C07D 239/20
[52] U.S. Cl. ..................................................... 544/334
[58] Field of Search ......................................... 544/334

[56] References Cited

U.S. PATENT DOCUMENTS

| | | | |
|---|---|---|---|
| 3,506,551 | 4/1970 | Beck et al. | 544/334 |
| 3,920,649 | 11/1975 | Beck et al. | 544/334 |
| 4,026,892 | 5/1977 | Beck et al. | 544/334 |

*Primary Examiner*—Nicholas S. Rizzo
*Attorney, Agent, or Firm*—Plumley & Tyner

[57] ABSTRACT

Process for the preparation of 2,4,5-trichloropyrimidine, characterized in that compounds of the formula

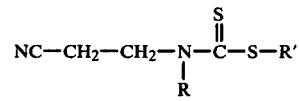

wherein
R a radical which can be split off under the reaction conditions and
R' an optionally substituted lower alkyl radical,
are reacted at temperatures from 0° to 50° C. with less than 7.5 mols of chlorine, in particular 3.5 to 7.0 mols of chlorine, and the reaction products are then afterheated to temperatures of 100°–150° C., in particular 110°–140° C., in the absence of chlorine.

4 Claims, No Drawings

PROCESS FOR THE PREPARATION OF 2,4,5-TRICHLOROPYRIMIDINE

The present invention relates to a new process for the preparation of 2,4,5-trichloropyrimidine.

The process is characterised in that (2-cyanoethyl)-dithiocarbamic acid esters of the formula

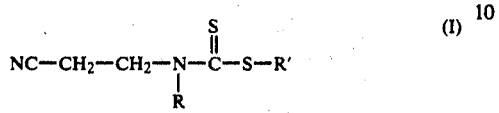

wherein
R denotes a radical which can be split off under the reaction conditions and
R' denotes an optionally substituted lower alkyl radical,
optionally mixed with an inert diluent, are reacted at temperatures from 0° to 50° C., preferably 30°-40° C., with less than 7.5 mols of chlorine, in particular 3.5-7.0 mols of chlorine, and the reaction products are then heated to temperatures of 100°-150° C., preferably 110°-140° C., in the absence of chlorine.

In a preferred embodiment, the chlorination is carried out at temperatures from about 20° C. to about 40° C. until the exothermic reaction has ended, and the reaction product is then after-heated to temperatures from 110° to 140° C. in the absence of chlorine.

Moreover, after heating to 100°-150° C., the reaction product can optionally be reacted again with elementary chlorine at 150°-200° C., preferably 160°-190° C. Sulphur-containing by-products are thereby converted into 2,4,5-trichloropyrimidine, so that in some cases the yield can be increased.

Suitable radicals R which can be split off under the reaction conditions are, in particular, lower alkyl, preferably $C_1$-$C_4$-alkyl, such as methyl, ethyl, propyl and butyl, and furthermore lower alkenyl, in particular $C_2$-$C_4$-alkenyl, such as allyl, it being possible for these groups also to be substituted, for example by chlorine, $C_1$-$C_4$-alkoxy or optionally substituted phenyl.

Examples of suitable radicals of this type are chloroethyl, methoxyethyl, benzyl, phenylethyl, chloropropyl, dichloropropyl and methoxypropyl.

Methyl is particularly preferred.

Preferred suitable optionally substituted lower alkyl radicals R' are $C_1$-$C_4$-alkyl, such as methyl, ethyl, propyl and butyl, it being possible for these groups also to be substituted, for example by chlorine, $C_1$-$C_4$-alkoxy or optionally substituted phenyl.

Examples of suitable radicals of this type are chloroethyl, methoxyethyl, benzyl and phenethyl.

Methyl is particularly preferred.

The chlorine can be employed in the chlorination reaction either in the form of elementary chlorine or in the form of customary chlorinating agents, such as, for example, sulphur dichloride, sulphuryl chloride or phosphorus pentachloride. In this procedure, of course, corresponding amounts of chlorinating agents must be used, for example 2 mols of $SCl_2$ instead of 1 mol of $Cl_2$.

The starting compounds of the formula (1) are indeed unknown, but they can be easily prepared according to statements in the literature for the preparation of dialkyldithiocarbamic acid alkyl esters (for example J. Chem. Soc. 1944, page 151), by a process in which, according to the following equation

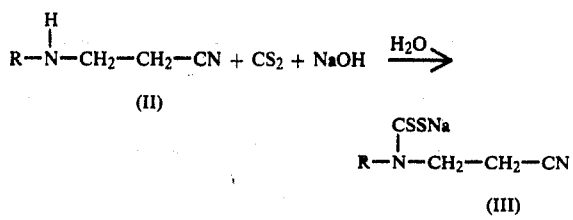

cyanoethylated amines (II), in which R has the abovementioned meaning, are reacted with carbon disulphide in aqueous sodium hydroxide solution to give the dithiocarbamates of the formula (III), which are then converted into the esters of the formula (I) by alkylation, for example with (substituted) alkyl halides, sulphonic acid alkyl esters or dialkyl sulphates, for example with dimethyl sulphate, according to the following equation:

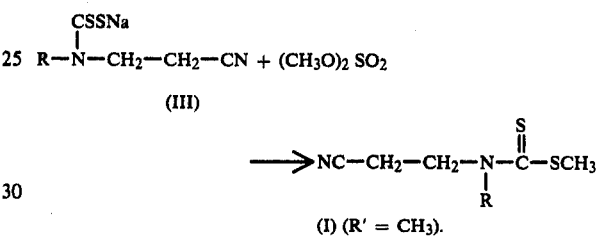

The cyanoethylated amines (II) are obtained, for example, by a process in which, according to the following equation

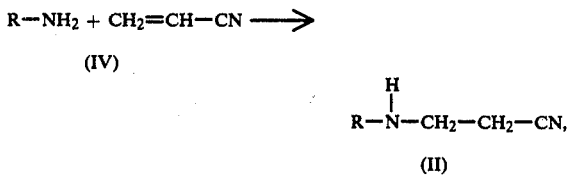

primary amines (IV), in which R has the abovementioned meaning, are added onto acrylonitrile; (compare, for example, J. Am. Chem. Soc. 66, 725 (1944); J. Am. Chem. Soc. 68, 1217 (1946); J. Am. Chem. Soc. 78, 2573 (1956) and J. Heterocyclic Chem. 1, 260 (1964).

Examples of (2-cyanoethyl)-dithiocarbamic acid esters of the formula (I) which are suitable for the process according to the invention are: (2-cyanoethyl)-methyl-dithiocarbamic acid methyl ester, (2-cyanoethyl)-ethyl-dithiocarbamic acid methyl ester, (2-cyanoethyl)-methyl-dithiocarbamic acid ethyl ester, (2-cyanoethyl)-ethyl-dithiocarbamic acid ethyl ester, (2-cyanoethyl)-methyl-dithiocarbamic acid propyl ester, (2-cyanoethyl)-methyl-dithiocarbamic acid butyl ester, (2-cyanoethyl)-methyl-dithiocarbamic acid chloroethyl ester, (2-cyanoethyl)-methyl-dithiocarbamic acid benzyl ester, (2-cyanoethyl)-butyl-dithiocarbamic acid methyl ester, (2-cyanoethyl)-benzyl-dithiocarbamic acid methyl ester and (2-cyanoethyl)-benzyl-dithiocarbamic acid benzyl ester.

Diluents which are inert under the reaction conditions are all the solvents which are resistant towards chlorine, for example chlorinated aliphatic and aromatic hydrocarbons, such as methylene chloride, chloroform, carbon tetrachloride, 1,1,2,2-tetrachloroethane, tetrachloroethylene, 1,1,2,3,3-pentachloropropane, hexachlorocyclopentadiene, octachlorocyclopentene, 1,2,4-trichlorobenzene, chlorinated pyrimidines and phosphorus oxychloride. In general, 0.5 to 20, preferably 1 to 10, parts by volume of diluent are used per part by weight of (I).

In the case where the chlorinating agent is a liquid under the reaction conditions, such as, for example, sulphur dichloride or sulphuryl chloride, the additional use of an inert diluent can be dispensed with.

Disulphur dichloride can be particularly advantageously used as the diluent in association with sulphur dichloride as the chlorinating agent.

If chlorine is used as the chlorinating agent, the reaction proceeds strongly exothermically initially. It is therefore appropriate not to use an excess of chlorine, in particular in the case of relatively large batches, until the exothermic reaction has subsided. After the strongly exothermic initial chlorination phase has subsided, it is appropriate to use an excess of chlorine (which can be detected by the greenish colour of the chlorination off-gas), in order to bring the reaction to completion as rapidly as possible.

In detail, the process is carried out by first mixing a (2-cyanoethyl-dithiocarbamic acid ester of the formula (I), in particular (2-cyanoethyl)-methyl-dithiocarbamic acid methyl ester, with one of the diluents mentioned, for example chloroform, at room temperature and then adding the chlorinating agent. External cooling and metering of the chlorinating agent are thereby matched with one another such that the initially strongly exothermic reaction does not become too vigorous and the temperature does not exceed 40° C.

Preferably, the chlorination is carried out at 30°-40° C. until the exothermic reaction has completely subsided.

The chlorine still dissolved in the reaction mixture and the sulphur chloride formed by the chlorination reaction are then stripped off in vacuo below 40° C., and the residue is heated further, either in vacuo or under normal pressure, with the exclusion of moisture, up to about 120°-130° C., 2,4,5-trichloropyrimidine being formed. The 2,4,5-trichloropyrimidine is separated off by distillation, for example with the aid of a Ag-mirrored packed column of about 1 m length. It can be readily obtained in a purity of over 99%.

If a chlorinating agent which is liquid under the reaction conditions is used, such as sulphur dichloride, it is advisable to initially introduce the chlorinating agent and to meter in the starting material (I) in portions at 30°-40° C.

If sulphur dichloride is used as the chlorinating agent it is particularly advantageous to initially introduce less than 15 mols of $SCl_2$ per mol of (I) (corresponding to less than 7.5 mols of $Cl_2$ per mol of (I), as mentioned above). The removal of excess chlorinating agent in vacuo below 40° C. is thereby dispensed with.

2,4,5-Trichloropyrimidine is a suitable starting component for the preparation of reactive dyestuffs (reaction with dyestuffs containing amino groups).

2,4,5-Trichloropyrimidine can be converted into tetrachloropyrimidine by gas phase chlorination (British patent specification No. 1,201,228). Tetrachloropyrimidine is a suitable reactive component for the preparation of reactive dyestuffs (compare, for example, Belgian patent specification No. 578,933). Moreover, 2,4,5-trichloropyrimidine has fungicidal and sporicidal properties (compare U.S. Pat. No. 3,227,612).

EXAMPLE 1

670 g (6.5 mols) of sulphur dichloride and (as the diluent) 250 ml of disulphur dichloride are initially introduced into a 2 l three-necked flask, which is provided with a stirrer, dropping funnel and thermometer, at 35° C. 87 g (0.5 mol) of molten (2-cyanoethyl)-methyl-dithiocarbamic acid methyl ester are now added dropwise in the temperature range from 35° to 40° C. in the course of half an hour, whilst stirring and occasionally cooling with ice-water. After the addition has ended, stirring is continued at 35°-40° C. for about a further quarter of an hour until the evolution of gas has ended. The reaction mixture is then heated to the reflux (137° C.) in the course of about 2 hours, whilst stirring, whereupon a thick precipitate forms in the temperature range from about 60° C. and redissolves from about 120° C. The formation of the 2,4,5-trichloropyrimidine has ended when a clear solution is present and no further evolution of gas is observed. All the constituents of the reaction mixture which can be distilled up to a bath temperature of 150° C./14 mm Hg are then distilled off. According to analysis by gas chromatography, the distillate contains 78 g (corresponding to 85% of theory) of 2,4,5-trichloropyrimidine.

If a stream of chlorine in slight excess (which can be detected from the greenish colour of the off-gas) is passed into the distillation residue from 150° C. up to an internal temperature of about 180° C. for ½-1 hour and all the constituents which can be distilled are then distilled off under a waterpump vacuum up to a bath temperature of 200° C., according to analysis by gas chromatography a further 4 g (corresponding to about 4% of theory) of 2,4,5-trichloropyrimidine are obtained.

By rectification of the product on a Ag-mirrored packed column of 1 m length, 2,4,5-trichloropyrimidine is obtained at boiling point$_{12}$ 94°-96° C. in a purity of over 99%.

The starting material (2-cyanoethyl)-methyl-dithiocarbamic acid methyl ester was obtained as follows:

420 g (5.0 mols) of 3-methylamino-propionitrile are first allowed to run into a solution, cooled to 5° C., of 203 g (5.07 mols) of sodium hydroxide in 1,800 ml of water, whilst cooling externally with ice/water, and thereafter 400 g (5.26 mols) of carbon disulphide are allowed to urn in in the course of about 10 minutes. The mixture is then further stirred vigorously for about 1.5 hours, whilst further cooling in an icebath, a virtually homogeneous phase being formed. 650 g (5.16 mols) of dimethyl sulphate are now added dropwise, whilst further cooling with ice, at a rate such that the reaction temperature does not exceed about 30° C. Thereafter, the oily layer which separates out is washed thoroughly with water, after which it solidifies to a colourless crystalline mass consisting of pure (2-cyanoethyl)-methyldithiocarbamic acid methyl ester. After filtering off and drying the product, it has a melting point of 45° to 46° C. The compound shows a characteristic IR spectrum with the following bands (in cm$^{-1}$): 2,250, 1,490, 1,425, 1,380, 1,300, 1,250, 1,195, 1,100, 1,030, 985, 955 and 755.

EXAMPLE 2

The procedure followed is analogous to that in Example 1, including the after-chlorination at 150°-180° C., with the difference that only 360.5 g (3.5 mols) of sulphur dichloride are initially introduced instead of 670 g (6.5 mols) of sulphur dichloride. According to analysis by gas chromatography, the distillates contain a total of 51.6 g (corresponding to 56.3% of theory) of 2,4,5-trichloropyrimidine.

We claim:

1. Process for the preparation of 2,4,5-trichloropyrimidine, characterised in that compounds of the formula

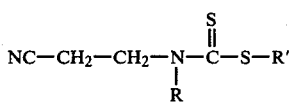

wherein

R a radical which can be split off under the reaction conditions and

R' an optionally substituted lower alkyl radical, are reacted at temperatures from 0° to 50° C. with less than 7.5 mols of chlorine, in particular 3.5 to 7.0 mols of chlorine, and the reaction products are then after-heated to temperatures of 100°–150° C., in particular 110°–140° C., in the absence of chlorine.

2. Process according to claim 1, characterised in that the chlorination is carried out at temperatures from about 30° C. to about 40° C. until the exothermic reaction has ended, and the reaction products are then after-heated to temperatures of 110°–140° C. in the absence of chlorine.

3. Process according to claim 1, characterised in that after heating to 100°–150° C. in the absence of chlorine, the reaction products are after-chlorinated at 150°–200° C. with elementary chlorine.

4. Process according to claims 1, 2 or 3, characterised in that R and R'=$C_1$–$C_4$-alkyl, preferably methyl.

* * * * *